(12) United States Patent
Angelsen

(10) Patent No.: US 6,461,303 B2
(45) Date of Patent: Oct. 8, 2002

(54) METHOD OF DETECTING ULTRASOUND CONTRAST AGENT IN SOFT TISSUE, AND QUANTITATING BLOOD PERFUSION THROUGH REGIONS OF TISSUE

(76) Inventor: Bjorn Angelsen, Bugges veg 4B, N-7051 Trondheim (NO)

( * ) Notice: Subject to any disclaimer, the term of this patent is extended or adjusted under 35 U.S.C. 154(b) by 12 days.

(21) Appl. No.: 09/766,328

(22) Filed: Jan. 19, 2001

(65) Prior Publication Data

US 2001/0056236 A1 Dec. 27, 2001

Related U.S. Application Data

(60) Provisional application No. 60/176,888, filed on Jan. 19, 2000.

(51) Int. Cl.$^7$ ................................................ A61B 8/14
(52) U.S. Cl. ........................................................ 600/458
(58) Field of Search ................................ 600/437, 407, 600/440–447, 449–459, 438; 424/9.51, 9.52, 450; 73/625, 626, 630, 631; 367/7

(56) References Cited

U.S. PATENT DOCUMENTS

| | | | | |
|---|---|---|---|---|
| 5,577,505 A | * | 11/1996 | Brock-Fisher et al. | ...... 600/458 |
| 5,706,819 A | * | 1/1998 | Hwang et al. | ............... 600/458 |
| 5,735,281 A | * | 4/1998 | Rafter et al. | ................. 600/458 |
| 5,776,063 A | * | 7/1998 | Dittrich et al. | ............. 600/408 |
| 5,833,613 A | * | 11/1998 | Averkiou et al. | ........... 600/440 |
| 5,961,464 A | * | 10/1999 | Poland | ........................ 600/458 |
| 6,132,377 A | * | 10/2000 | Bolorforosh et al. | ........ 600/458 |
| 6,146,657 A | * | 11/2000 | Unger et al. | ................. 424/450 |
| 6,186,951 B1 | * | 2/2001 | Lizzi et al. | .................. 600/458 |
| 6,213,951 B1 | * | 4/2001 | Krishan et al. | ............. 600/458 |
| 6,231,834 B1 | * | 5/2001 | Unger et al. | ............... 424/9.51 |

* cited by examiner

*Primary Examiner*—Marvin M. Lateef
*Assistant Examiner*—Ali M. Imam
(74) *Attorney, Agent, or Firm*—Cohen, Pontani, Lieberman & Pavane

(57) ABSTRACT

A method for detection of ultrasound contrast agent in soft tissue according to the present invention includes utilizing an ultrasound transmit beam former and transducer array assembly for transmitting directive, focussed ultrasound pressure pulses with steerable transmit amplitude, transmit aperture, transmit focus, and transmit direction, and with temporal frequency components within a limited band B centered at a frequency $f_0$, towards a region of soft tissue that contains ultrasound contrast agent bubbles. The transmit pulse parameters are arranged, preferably using multiple transmit pulses, so that the incident pressure pulse that is utilized for imaging of the contrast agent for a particular depth, has minimal variation over the actual image range. The non-linearly distorted, back-scattered ultrasound signal is received from both the tissue and the ultrasound contrast agent bubbles with the same ultrasound transducer assembly and the received array element signals are passed through a receiver beamformer that has a steerable spatially directive receiver sensitivity.

23 Claims, 14 Drawing Sheets

METHOD OF DETECTING ULTRASOUND CONTRAST AGENT IN SOFT TISSUE, AND QUANTITATING BLOOD PERFUSION THROUGH REGIONS OF TISSUE

This application claims priority from Provisional application Ser. No. 60/176,888, filed Jan. 19, 2000.

BACKGROUND OF THE INVENTION

1. Field of the Invention

The present invention is directed to a method for detecting an ultrasound contrast agent in a soft tissue and quantitating blood perfusion through regions of tissue by detecting the contrast agent in the tissue.

2. Description of the Related Art

An ultrasound contrast agent is a solution of small gas bubbles (diameter ~5 $\mu$m) that is injected into the blood stream. Such bubbles show strong and non-linear scattering of ultrasound at the frequencies used for medical ultrasound imaging. Medical applications of the contrast agents include, but are not limited to, enhancing imaging of blood vessels, improving the detection of the endocardium as a border of the ventricular cavities, and improving the detection of blood jets through leaking cardiac valves or septal defects.

There has also been great hopes that ultrasound contrast agent should be able to detect and quantify blood perfusion through the tissue, especially the myocardial tissue where coronary disease strongly influences the myocardial perfusion. The widespread occurrence of coronary artery disease as a major cause of death in the western world has made this application of the contrast agents and methods for detection of the contrast agents in the tissue a target for development of various types of ultrasound contrast agents.

Second harmonic ultrasound imaging, is today the commonly used method for detecting and imaging ultrasound contrast agent in the tissue. The non-linear elastic properties of the contrast agent bubbles produce higher harmonic components and sub harmonic components of the transmitted pulse frequency band in the scattered signal directly in the scattering process. However, with the present wideband transducer technology it is only possible to utilize the second harmonic component of the signal by transmitting an ultrasound pulse with frequency spectrum in the lower part of the active frequency band of a wideband transducer. The second harmonic component of the scattered signal is then received in the upper part of the transducer frequency band.

Forward propagation of the ultrasound pulse through the tissue produces a distortion of the pulse due to pressure dependent propagation velocity. The distortion is limited by acoustic power absorption in the tissue, so that in practice we get high enough amplitude of the 2nd harmonic band in the pulse to use this harmonic band for imaging of soft tissue itself. With venous injection of contrast agent, the 2nd harmonic frequency band of the scattered signal from the myocardial tissue has, however, comparable amplitude to the 2nd harmonic frequency band of the signal from contrast agent in the myocardium. The back scattered tissue signal then represents a background noise for the detection of the contrast agent, and hence limits the detectability of low concentrations of the agent based on the 2nd harmonic component of the back scattered signal.

The non-linear elasticity of the contrast agent is much stronger than that of the tissue. Accordingly, considerable distortion of the scattered pulse directly in the scattering process results with high amplitudes in the 3rd and 4th harmonic component of the incident pulse frequency band. More importantly, the scattered amplitudes from the contrast agent in these frequency bands are much stronger than the scattered amplitudes in the 3rd and 4th harmonic frequency bands from the tissue. Therefore, the use of harmonic frequency bands higher than the 2nd component of the transmitted pulse frequency band for detection and imaging of the contrast agent provides improved separation between the signal amplitudes from the contrast agent and the signal amplitudes from the tissue.

There are however several practical problems in utilizing the 3rd and 4th harmonic component of the transmitted frequency band for detection and imaging of ultrasound contrast agent, as well as using such imaging to grade the degree of blood perfusion through tissue:

The first problem is that the present medical ultrasound transducers have so narrow a bandwidth that it is not possible to transmit a pulse with frequency band around $f_0$, and receive back-scattered frequency components in the frequency bands around $3f_0$ and $4f_0$ with adequate sensitivity. Adequate wideband transducers have been made by highly damping the transducers, but this reduces the sensitivity to the signal scattered from the contrast agent in the myocardium below tolerable limits. According to the present invention, a transducer is used with capabilities of transmitting frequencies in a band around $f_0$, with high sensitivity in the receive band around the 3rd or 4th harmonic component of the transmit band. In the particular implementation of the invention, the high receive sensitivity is obtained by using resonant operation of the transducer in the receive band with minimal dampening.

For the invention to fully work, the transmitted pulse must have sufficiently limited amplitude in the receive frequency bands. A solution to this problem is presented according to the invention by either bandpass filtering the transmitted pulse both in the transducer and/or electrically before driving the transducer, or by using band limited pulse generator with linear drive amplifiers of the array transducer elements.

A second problem associated with utilizing the 3rd and 4th harmonic component of the transmitted frequency band for detection and imaging of ultrasound contrast agent is that the pulse distortion in the scattering from the contrast agent bubbles, highly depends on the amplitude of the pulse incident on the bubble. Absorption of the transmitted pulse attenuates the incident amplitude with depth, depending on the transmitted frequency $f_0$. In addition, the beam divergence past the transmit focus will produce an amplitude attenuation with depth. In the normal imaging situation, the amplitude of the transmitted pulse hence attenuates with depth, giving a subsequent reduction in the distortion of the scattered pulse from the contrast agent with depth. This produces a depth variable detection of the contrast agent, and presents severe problems for imaging and quantitation of regions of reduced blood perfusion in the myocardium.

The power absorption in the tissue considerably reduces with the frequency, being approximately 0.5 dB/cmMHz. Hence, by using a low transmitted center frequency at for example $f_0$=0.875 MHz, the total absorption attenuation from 2–10 cm is ~3.5 dB. Geometric focussing of the beam to the far end of the image range may be used to compensate for this absorption attenuation. Due to diffraction at such low frequencies, the maximal amplitude in the focussed beam is found closer to the transducer than the geometric focus. By locating the geometric transmit focus beyond the image range, at for example 12 cm, the transmit beam focussing will give a gain of ~3.4 dB from 2–10 cm with a 18 mm circular aperture. Hence, by using sufficiently low transmit frequency, one can obtain approximately constant incident amplitude over a limited image range by proper selection of transmit aperture and focus.

A transmit center frequency of 0.875 MHz, gives 3rd and 4th harmonic center frequencies at 2.625 MHz and 3.5 MHz, which are typical frequencies used for cardiac imaging. These frequencies produce tolerable absorption attenuation of the backscattered signal so that it can be compensated for by a depth variable receiver gain. A receive frequency in the range of 2.5–4 MHz also gives a lateral resolution of the receive beam comparable to that with regular echocardiography.

To obtain a narrower transmit beam at all ranges and to further improve the equalization of the incident pulse amplitude with depth according to the invention, the depth along the receive beam is divided into sub-ranges. Each sub-range is observed at different time intervals with different transmit pulses, where the focus of each transmit pulse is located within the corresponding receive range, and both the transmit focus, the transmit amplitude, and the transmit aperture are adjusted for optimal equalization of the incident pulse amplitude within the corresponding receive range, under the actual absorption of the ultrasound in the tissue.

To cover a range from, for example, 2 cm to 15 cm with minimal variation of the incident pulse according to the invention, the range could be divided into subranges from 2–6 cm to be interrogated with a transmit pulse with focus at 7 cm with a reduced transmit aperture to secure sufficient focal depth, followed by a 2nd transmit pulse focussed at say 18 cm, using larger transmit amplitude and transmit aperture to achieve the same incident pulse amplitude at 2 and at 15 cm. Further detailed optimization of number of transmit pulses, with corresponding transmit foci, amplitudes, and apertures can be done within the scope of the invention. Pulse destruction by the transmit pulses must also be taken into the account in this optimization, as described below.

A third problem associated with utilizing the 3rd and 4th harmonic component of the transmitted frequency band for detection and imaging of ultrasound contrast agent is that the power of the received signal from a depth, is proportional to the concentration of contrast agent in the tissue. The source of contrast agent in a region of the myocardium is the inflow of blood to the region with a sink of contrast agent produced by the venous outflow. In the stationary situation with some blood flow through the tissue, the concentration of contrast agent in a tissue region is hence given by the product of the blood concentration in the region and the concentration of contrast agent in the inflowing blood. The contrast agent concentration will in this situation not be reduced before close to complete blocking of the blood flow to the region occurs. Therefore, in a stationary situation, the received signal power from a range will give limited quantitative grading of the perfusion through the tissue region.

One method to improve the grading of the perfusion is to introduce an additional sink of contrast agent in the region such, for example, as by destroying the contrast agent with high amplitude incident ultrasound pressure pulses. Partial destruction of the contrast agent will give a concentration that depends on both the inflow rate of blood to the region (i.e., the source of contrast agent) and the destruction rate (i.e., the additional sink of contrast agent). The concentration of contrast agent will in this case quantitatively be reduced with reduced blood perfusion in the tissue. By comparing the signal level from one region with the signal level from regions with normal perfusion, the received signal level will give a quantitative measure of regionally reduced perfusion. With complete destruction of the contrast agent in the image region, one can use the re-filling time of contrast agent in the tissue as a quantitative measure of the perfusion through the tissue.

It is then important that the whole image range is imaged with incident pulses of equal amplitude so that variations in backscattered amplitude are produced by variations in the concentration of contrast agent and not by variations in the incident pulse amplitude. As some destruction occurs at practical image amplitudes, it is also important to design the transmit pulses so that this destruction is the same throughout the whole image range.

Also, when transmitting dedicated destruction pulses for partial destruction of the contrast agent to quantitatively grade the perfusion, one must assure that the degree of destruction is practically constant throughout the whole image range. The amplitude of the destruction pulses can be depth tailored as for the image pulses, using multiple transmit pulses with optimized transmit foci, amplitudes, and apertures. The pulse with focus in one sub-range, will then provide some contrast agent destruction at other ranges, and the whole set of transmit pulses for each image direction, must be designed for equal and limited destruction of the contrast agent along the whole image depth.

Multiple foci destruction pulses will also provide minimal width of the destruction beam for all depths, ensuring that the destruction pulses for one image beam produce limited contrast agent destruction in neighboring image beams. Destruction pulses with narrow focus at small depths are then used first to destroy contrast agent at low ranges. The rapid geometric widening of the beam past the focus will then produce an attenuation of the destruction pulse which reduces contrast agent destruction at larger depths. Using a higher frequency of the shallow range destruction pulses, will also increase the attenuation of these pulses at deeper ranges. The destruction of the contrast agent at deeper ranges, is then followed up with new destruction pulses with deeper foci, larger transmit amplitudes and apertures, and possible lower center frequency. The overlap of destruction from the pulses at all ranges must be taken into account. Therefore, the whole set of destruction pulses must be designed for each receive beam direction so that even destruction of the contrast agent over the whole image range occurs.

Contrast agent destruction by neighboring beams will only complicate the imaging at the edges of the scan, where the edge beam has a single neighbor. Further into the image, all beams will get the same destruction by the neighboring beams.

SUMMARY OF THE INVENTION

A method for detection of ultrasound contrast agent in soft tissue according to the present invention includes utilizing an ultrasound transmit beam former and transducer array assembly for transmitting directive, focussed ultrasound pressure pulses with steerable transmit amplitude, transmit aperture, transmit focus, and transmit direction, and with temporal frequency components within a limited band B centered at frequency $f_0$, towards a region of soft tissue that contains ultrasound contrast agent bubbles. The transmit pulse parameters are arranged, possibly using multiple transmit pulses, so that the incident pressure pulse that is utilized for imaging of the contrast agent for a particular depth, has minimal variation over the actual image range. The non-linearly distorted, back-scattered ultrasound signal is received from both the tissue and the ultrasound contrast agent bubbles with the same ultrasound transducer assembly and the received array element signals are passed through a receiver beamformer that has a steerable spatially directive receiver sensitivity.

The transducer assembly has high sensitivity at the receive band of frequencies centered at $3f_0$ and/or $4f_0$ for maximal sensitivity of the distorted, non-linearly scattered signal from the contrast agent bubbles. The received signal is high-pass filtered so that the lowest frequency component of the resulting signal is at least 2 times higher than the frequency component of the transmitted signal. The amplitude of the high-pass filtered signal is used for detecting ultrasound contrast agent bubbles buried within the tissue, and for imaging of contrast agent bubbles in the tissue.

The depth variation of the amplitude of the incident pressure pulse is minimized by positioning the transmit focus deeper than the image range.

The width of the incident beam at each location is reduced, and the depth variation of and amplitude of the incident pressure pulse is minimized by dividing the total imaged depth range into sub-ranges, where a separate transmit pulse is used to interrogate each sub-range consecutively in time, arranging the transmit focus, the transmit aperture, and the transmit amplitude for each pulse so that the pressure pulse amplitude incident on the contrast agent bubbles at their location in the absorbing tissue is practically equal for each sub range.

The transmitted center frequency $f_0$ can be less than 1 MHz in the preferred embodiment.

To improve the sensitivity of the receiving transducer assembly in the receive band, a backing mount of the transducer with characteristic acoustic impedance less 30% of that of the active electro-acoustic layer may be used. Alternatively, the improved sensitivity of the receiving transducer assembly in the receive band may be facilitated by using a backing mount of the transducer with characteristic acoustic impedance greater than 150% of that of the active electro-acoustic layer.

The sensitivity of the receiving transducer assembly in the receive band is also facilitated by making the transducer assembly resonant in this band.

The ultrasound transducer array comprises an electro-acoustic active layer divided into several transducer elements with a front and a back face, a 1st thin electrode layer covering the front face, and a 2nd thin electrode layer covering the back face. The electrodes are electrically connected to electric terminals for coupling of energy between the electric terminals and acoustic vibrations in the transducer elements.

A substrate layer is mounted on the back side of the acoustic layer with approximately the same acoustic properties as the active layer. The back layer is mounted on an acoustically absorbing backing with acoustic impedance much lower than the two layers.

The ultrasound transducer array further comprises at least one acoustic matching layer mounted on the front face of the active layer and acoustically in contact with the tissue. The acoustic properties and thicknesses of the matching layers are adjusted to facilitate improved acoustic power transfer to and from the tissue and to facilitate a wide bandwidth of the electro-acoustic transfer function to transmit a band-limited ultrasound pulse centered at $f_0$ into the tissue, and to receive backscattered ultrasound pulses in the 3rd or 4th harmonic component, or both, of the transmit band. The substrate layer also is electro-acoustically active and divided into individual transducer elements with common faces to the first transducer elements, with a third, thin electrode layer on the back face of the elements, which can be combined with the 2nd or the 1st electrodes for coupling of energy between the electric terminals of the electrodes and acoustic vibrations in the transducer combined transducer elements.

Two of the 3 electrode layers may be connected to the transmit amplifiers to transmit the low frequency acoustic pulse, and another two of the 3 electrode layers may be coupled to the receiver amplifiers to receive the back scattered acoustic energy from the contrast agent bubbles.

The method for detecting the contrast agent may be used for quantitating variations in tissue blood perfusion. To accomplish this, the ultrasound contrast agent in the tissue may first be destroyed uniformly with depth and direction in the tissue with a controllable degree, followed by imaging of the backscattered signal power from contrast agent in the tissue.

Partial destruction of the contrast agent may be performed so that the amplitude of the backscattered signal in the 3rd or 4th harmonic component of the transmit frequency band gives a regional grading of the perfusion.

Separate destruction pulses may be used to controllably destroy the contrast agent uniformly over the whole image field.

The contrast agent may also be fully destroyed in the tissue, and imaging may be performed at a time interval after this destruction, so that the amplitude of the back-scattered signal in the 3rd or 4th harmonic component of the transmit frequency band gives a regional grading of the refilling time of blood into the tissue, and hence the blood perfusion through the tissue.

The timing of the contrast agent destruction may be derived from the electrocardiogram (ECG), and imaging may be performed at a selected period in the cardiac cycle derived from the ECG.

The increase in image intensity is followed for many heart cycles after the contrast destruction to obtain complete re-filling curves of contrast agent into different regions of the tissue, for regional grading of the perfusion into the tissue.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The stiffness of a soft tissue increases when the tissue is compressed by the positive pressure in a transmitted ultrasound pulse. The propagation velocity of an ultrasound wave therefore increases with positive pressure due to this stiffness increase. Similarly, the propagation velocity decreases with negative pressure in the incident pulse. The positive pressure swing 101 of the initial transmitted ultrasound pressure pulse in FIG. 1a hence propagates faster than the negative swing 102. After a propagation distance, we therefore get a distortion of the pressure pulse, for example illustrated as the dotted curve 103. The distortion of the pulse increases with the propagation distance.

Figure 1B:
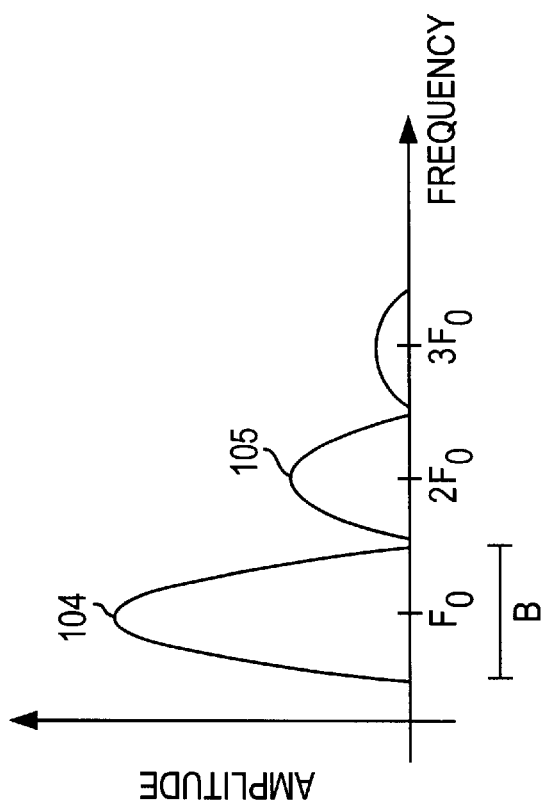
FIG. 1*a* is a graph showing the transmitted and the propagation distorted pressure pulse and FIG. 1*b* shows the Fourier amplitude spectrum of a typically distorted pulse in tissue.
Figure 1A:
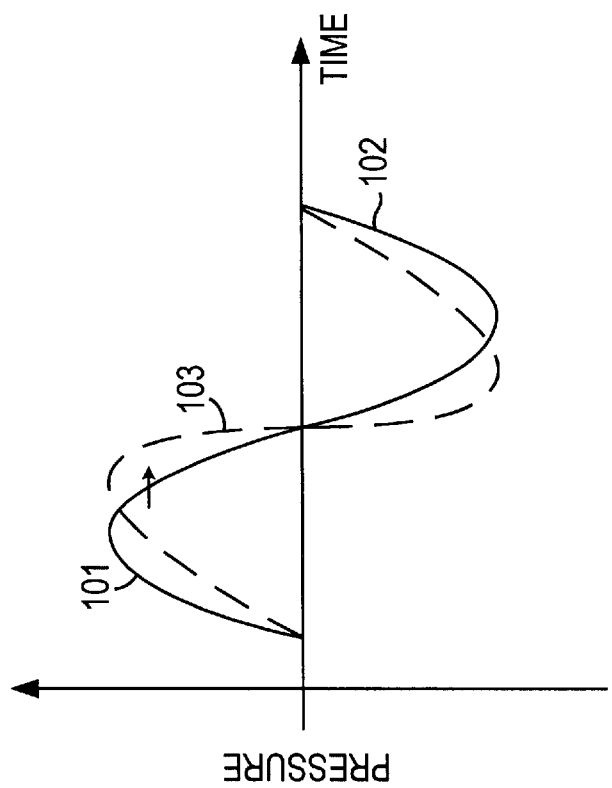

With no acoustic power absorption, the peak of the wave will eventually catch up with the trough, producing what is termed acoustic shock. However, the pulse distortion introduces higher harmonic frequency components in the pulse, with much larger absorption attenuation than the fundamental component. This limits the pulse distortion in the tissue, giving a focal pulse with a typical Fourier amplitude spectrum as shown in FIG. 1b. The Figure displays a first harmonic band 104 with bandwidth B and centered around the center frequency $f_0$ of the transmitted pulse. A $2^{nd}$ harmonic band 105 centered around $2f_0$ has lower amplitude than the $1^{st}$ harmonic band, and a $3^{rd}$ harmonic band 105 centered around $3f_0$ is barely visible above the noise level. The $4^{th}$ harmonic band disappears below the noise.

For a short duration pulse (couple of oscillations), the distortion also produces sub harmonic frequency components from the time derivative of the pulse envelope. For typical ultrasound pulses, this sub harmonic frequency band is centered at approximately $f_0/2$. The sub harmonic frequency band also interacts with the transmitted and the harmonic frequency bands to produce supra harmonic frequency bands centered at approximately $(n\pm\frac{1}{2})f_0$, with n=1, 2, 3, . . . , but these bands are weak and hardly visible above the noise. Due to the lower frequency of the sub harmonic component, it has less absorption attenuation than the higher harmonic bands, and can be relatively dominating in the wave for extreme depths (deeper than what is found in the body), creating a phenomenon called "old age".

The generation of higher harmonics in the oscillation is reduced with increased wavelength, as the distance for the peak of the pressure to catch up with the trough increases. The relative production of harmonic content in the wave therefore decreases with $f_0$, as does also the power absorption in the wave. For a given depth, we therefore have an optimal $f_0 = f_{n,max}$ for maximal generation of the nth harmonic component in the tissue.

The $2^{nd}$ harmonic component of the transmitted frequency band in the back scattered signal from soft tissue, stems from the non-linear, forward propagation distortion of the incident pulse, and linear back scattering of the distorted pulse. The amount of $2^{nd}$ harmonic component in the back-scattered signal from the tissue inhomogeneities, therefore, depends on the forward propagation distortion of the incident pulse.

For the contrast agent bubbles, the situation is different, in that considerable non-linear distortion of the incident pulse occurs in the scattering process itself Since the bubble is much smaller than the acoustic wavelength (bubble diameter ~5 μm, acoustic wavelength ~500 μm), the bubble volume can expand with mainly shear deformation of the surrounding tissue (i.e. limited volume change). This phenomenon produces the following effects on volume compression/expansion of the bubble and the nearest surrounding tissue:

i) The volume compressibility of the bubble with nearest surrounding tissue is determined mainly by the compressibility of the bubble, where a co-oscillating volume of tissue approximately 3 times the bubble volume moves in the compression, with mainly shear deformation. This produces an oscillation resonance of the bubble diameter, determined by the interaction of the co-oscillating mass of the surrounding tissue, and the elasticity of the bubble.

ii) The bubble has a highly non-linear elasticity given by the adiabatic gas relation and the non-linear elasticity of the bubble shell. This means that a negative acoustic pressure will give a relatively large increase in the bubble diameter, as the gas pressure does not become negative. When the pulse pressure starts to swing positive, the mass of the surrounding tissue gets a high inward momentum, which interacts with the bubble elasticity to generate a high, non-linear increase in the pressure.

Figure 2B:
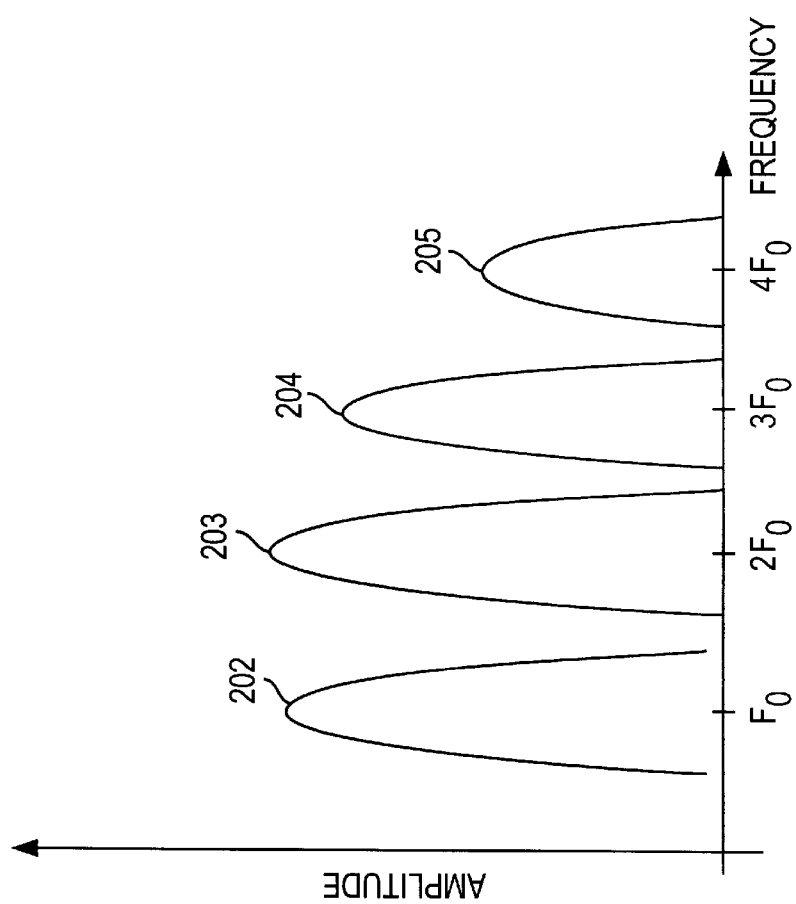
FIG. 2*b* shows the Fourier amplitude spectrum of the pulse.
Figure 2A:
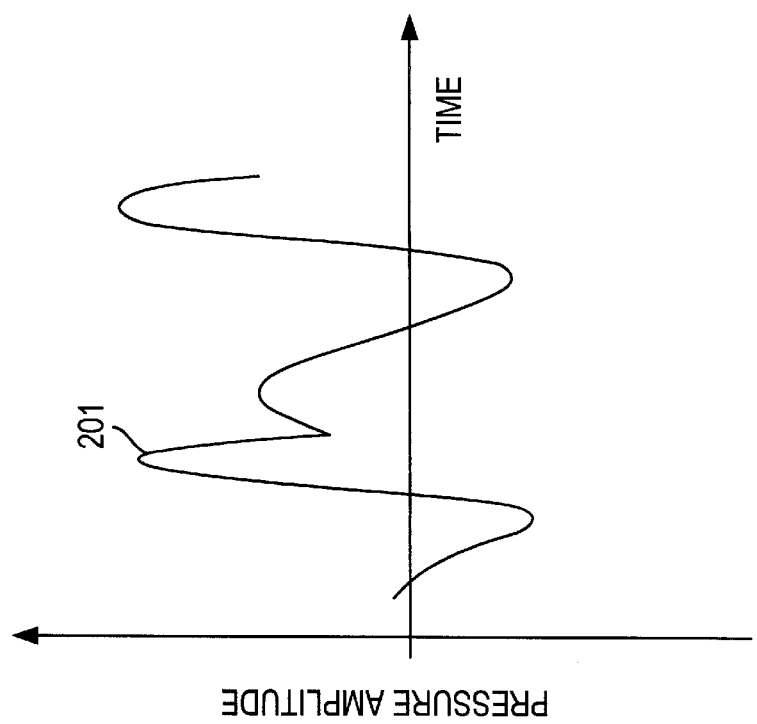
FIG. 2*a* is a graph showing a typical, distorted backscattered pulse from a contrast agent bubble

The non-linearity of point ii) is the basic mechanism for harmonic generation in the scattering of ultrasound from contrast agent bubbles. By proper selection of the gas and bubble diameter, one can use the resonance effect in point i) to enhance the scattering of a selected harmonic component of the incident frequency band. When the bubble resonance frequency is slightly larger than the incident ultrasound frequency, large non-linear scattering of the incident ultrasound pulse occurs, with a typical back-scattered pulse illustrated in FIG. 2a as 201. The Fourier amplitude spectrum of this pulse is shown in FIG. 2b, displaying a $1^{st}$ harmonic band 202 around $f_0$, a $2^{nd}$ harmonic band 203 around $2f_0$, a $3^{rd}$ harmonic band 204 around $3f_0$, and a $4^{th}$ harmonic band 205 around $4f_0$. We notice that the drop of the amplitude of the $3^{rd}$ and $4^{th}$ harmonic band relative to the $1^{st}$ harmonic band is much less than for the tissue signal in FIG. 1b.

With the transmitted ultrasound frequencies used for $2^{nd}$ harmonic imaging of tissue today, ~1.7 MHz, the amplitudes of the $2^{nd}$ harmonic component from the tissue and from the contrast agent with venous injection from contrast agent, are comparable. Hence, with the weak signals obtained from contrast agent in the myocardium with venous injection of the contrast agent, the tissue signal appears as a background noise in the $2^{nd}$ harmonic band. Using the $3^{rd}$ and/or $4^{th}$ harmonic component of the transmitted frequency band in the back-scattered signal, hence improves the enhancement of the contrast agent signal above the tissue signal for the detection and imaging of the contrast agent.

In the selection of the transmitted frequency, one must lay as a basis that the selected harmonic component of the scattered signal from the contrast agent must return to the body surface with tolerable absorption. High amplitudes of the incident ultrasound pressure pulse destroy the contrast agent bubbles, setting a limit on the scattering source strength of the contrast agent. One hence must secure limited absorption of the scattered signal on its return from the scattering bubble to the receiving transducer. For the depth ranges found with noninvasive cardiac imaging of the adult population, this means receive frequencies in the range of approximately 2–5 MHz, 3.5 MHz being the most frequently used frequency. Using the $3^{rd}$ or the $4^{th}$ harmonic component of $f_0$ for detection of the contrast agent, $4f_0=3.5$ MHz gives $f_0=0.875$ MHz and $3f_0=3.5$ MHz gives $f_0=1.17$ MHz.

One would hence use transmitted frequencies $f_0$ around 1 MHz to utilize the $3^{rd}$ and/or $4^{th}$ harmonic component of the transmitted frequency band. One should note that with so low transmitted frequency, the $2^{nd}$ harmonic component from the tissue is reduced by ~10 dB, so that the detectability of contrast agent based on the $2^{nd}$ harmonic component improves. However, the $3^{rd}$ and $4^{th}$ harmonic frequencies gives reduced width of the receiver beam, reducing the lateral resolution in the final image.

Figure 3:
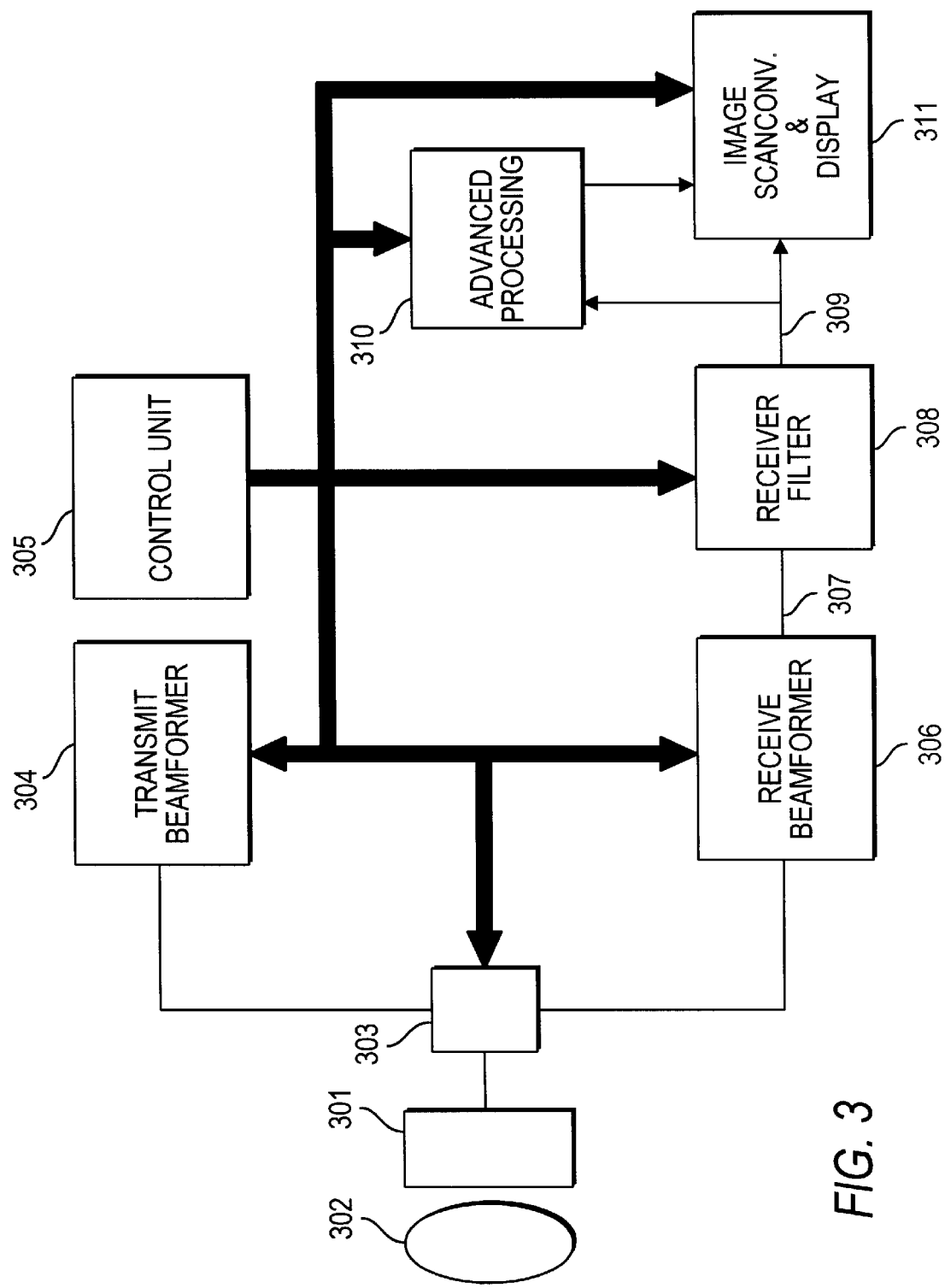
FIG. 3 is a block diagram of an instrument for real time imaging of contrast agent using higher harmonic components in the scattered signal for the detection and imaging of the contrast agent.

A block diagram of an instrument for real time implementation of the contrast agent detection method, is illustrated in FIG. 3. An array 301 with a plurality of ultrasound transducer elements, is via a transmit/receive switch 303 driven by a set of signal generators and power amplifiers that are part of a transmit beam former 304 built according to well known principles. The transmit beam former generates appropriate electric drive signals for the transducer array elements to steer with selectable transmit aperture both the direction, the focus, and the amplitude of a transmitted ultrasound pulse into soft tissue 302 that contains ultrasound contrast agent bubbles. The transmit beam former and transmit/receive switch is steered by the control unit 305, which after the pulse transmission switches 303 to connect the transducer array to a receiver beam former 306. The receiver beam former produces with range dynamic focussing the received ultrasound radio frequency (RF) signal 307 for a spatially directive receiver beam, or parts thereof, according to well known principles. The received RF-signal is then fed to a filter unit 308, which in its output 309 selects frequency bands of the received signal around harmonics of the transmitted center frequency. In a minimal version, the amplitude of 309 is fed to a scan converter and display unit 311. This unit displays according to well known principles, the amplitude of 309 as an M-mode, a two-dimensional or a three dimensional image depending on the ultrasound beam scan modes of the data collection. Hence, the second, third or fourth harmonic component of the transmit frequency band can be used for the detection and imaging of the contrast agent.

In a more advanced version, the filtered RF-signal 309 can be further processed in an advanced processing unit 310 to determine for example the temporal variation of the signal intensity to monitor refilling times of blood into a region. In other versions according to the invention, the filtered RF-signal 309 can undergo Doppler processing to determine the velocity of the contrast agent. Such processing can for example be used to suppress the contrast agent signal from the blood pools in the heart cavities in the periods of the heart cycle where the blood in the heart cavities moves faster than the myocardium. This can be used to enhance the display of the scattered contrast agent signal in the myocardium above the signal from the heart cavities, as described below. The Doppler processing can also be used to determine myocardial strain from gradients in the myocardial velocity or the phase of the RF-signal between consecutive pulses.

The transducer array assembly 301 in FIG. 3 must be able to transmit ultrasound frequencies in a limited frequency band B centered around $f_0$, and receive the back-scattered signal with frequency components in a frequency band around $3f_0$ and/or $4f_0$ with adequate sensitivity. Damping of the transducer in the transmit band around $f_0$ is tolerable within limits, as adequate amplitude of the transmitted pressure pulse can be achieved by increasing the electric drive voltage of the transducer. However, damping of the transducer in the receive band is highly disadvantageous, as it irreversibly reduces the detectability of contrast agent bubbles in the tissue.

As stated above, to avoid destruction of the contrast agent bubbles, the source strength of the scattering bubbles is limited. Hence, there is a maximal amplitude of the received contrast agent signal in the $3^{rd}$ and $4^{th}$ harmonic band, and it is therefore especially important that the internal damping (power absorption) of the transducer in the receive band is low. Such absorption directly drains power from the received signal, reducing the receive sensitivity and limiting the detectability of contrast agent bubbles in the tissue. To minimize the phase angle of the electric transducer input impedance in the receive band, and hence reduce reception power losses, it is advantageous to design mechanical resonance frequencies in the receive band, as is further described in the following.

Figure 4B:
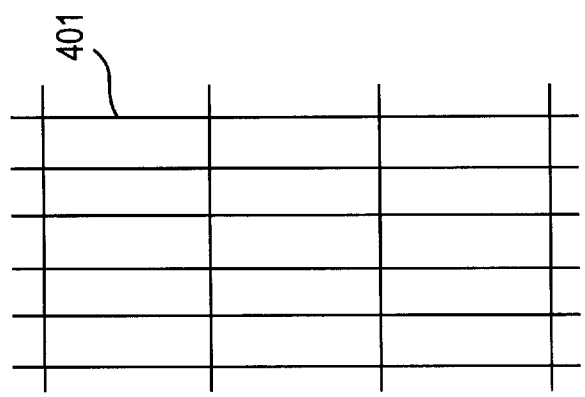
FIG. 4b shows a typical lateral division of the active layer into array elements in a two-dimensional matrix (the transducer is also useful for $1^{st}$ and $2^{nd}$ harmonic imaging)
Figure 4A:
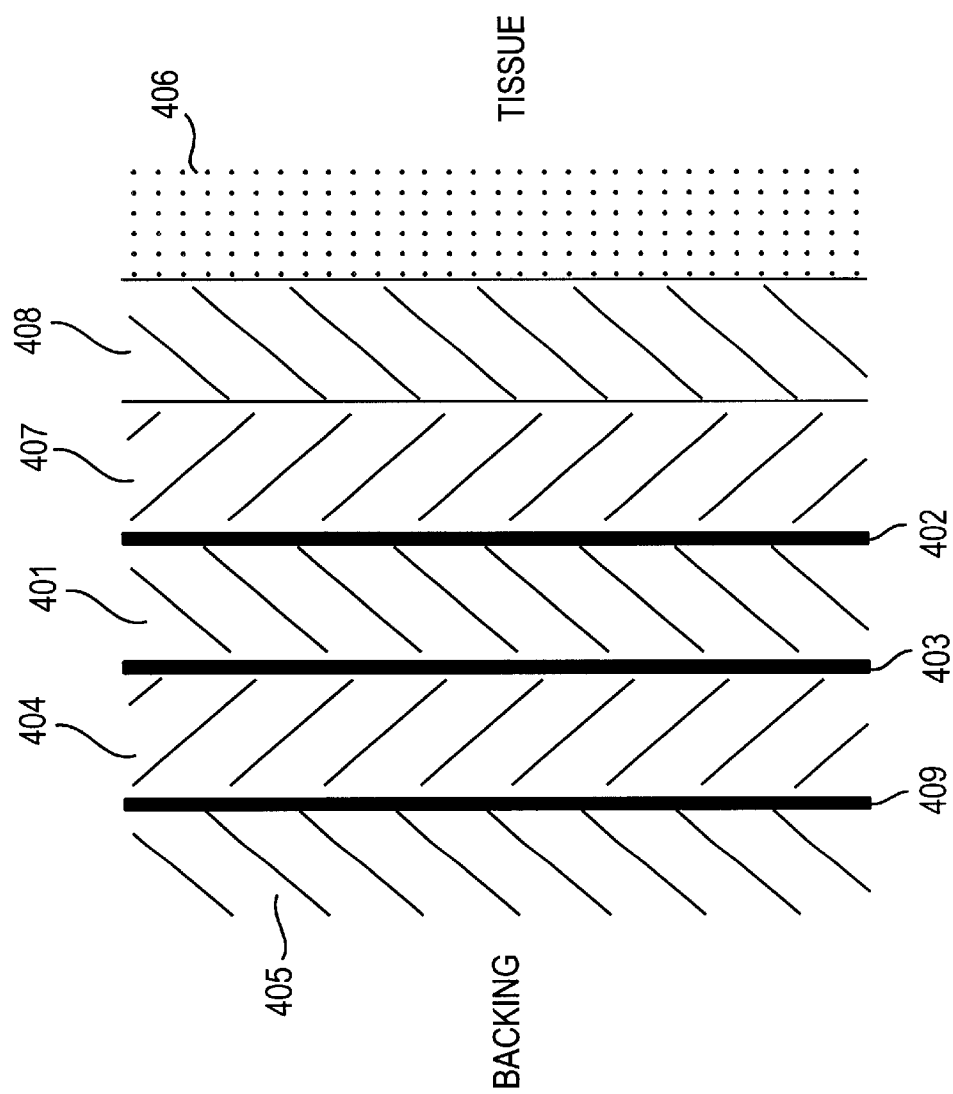
FIG. 4a is a cross section of a layered ultrasound transducer design with low damping due to low backing impedance, that can transmit an ultrasound pressure pulse with limited frequency band around $f_0$, and receive back scattered signal in a frequency band around the $3f_0$ and/or $4f_0$

An array transducer design that satisfies these requirements is shown in FIG. 4a. The transducer is a layered structure, composed of an electro-acoustic active layer 401 with a front electrode, 402, and a back electrode, 403. By placing a voltage across the electrodes, the layer thickness will contract or expand depending on the polarity of the voltage. The layer is laterally divided into a number of transducer elements, 410, where FIG. 4b illustrates a possible lateral division for a two-dimensional array. The elements have individual electrodes on at least one of the faces, so that the voltage across each element can be controlled individually. It is then convenient that the front electrode 402 is a ground layer, common for all elements, while the back electrode 403 is divided into individual electrodes for each transducer element. With this selection, the front ground electrode will provide shielding of the active elements against external electromagnetic interference.

The active layer 401 is mounted on an acoustic substrate layer 404, with similar characteristic acoustic impedance as the active layer. This substrate layer will influence transducer resonances both in the transmit and the receive bands, and is mounted on a backing material 405 with as low characteristic acoustic impedance as possible, while still giving mechanical support for the transducer. Reducing the characteristic impedance of the backing, reduces the acoustic power that is transferred into the backing and hence the transducer power losses, improving the transducer sensitivity.

In an alternative implementation of the invention, the added acoustic layer 404 is mounted in front of the active layer 401, still having a similar characteristic impedance as the active layer, which together forms a composite layer with high characteristic impedance that participates together to form resonances in the structure.

In still an alternative implementation according to the invention, the substrate layer is made of the same electroacoustic active material as the active layer 401, and the back face of each element is coated with an electrode 409, the use of which is discussed below.

Between the composite layer and the acoustic load material is mounted a set of acoustic impedance matching layers which couples acoustic energy from the active layer 401 to the tissue 406. One typically will use two acoustic matching layers 407 and 408, as shown in the Figure.

A typical selection of parameters for the transducer, is to use a ceramic-epoxy composite for the acousto-active layer, which is made according to well known principles. One can then typically obtain a characteristic impedance of the active layer of $Z_x=10$ MRayl. A typical value of the relative dielectric constant at fixed strain is $\epsilon_{33}^S=400$, and the value of the piezoelectric h-parameter is $h_{33}=20*10^8$ V/m. The thickness of the active layer is chosen so that it has a short circuit $0.19\lambda$ at 3 MHz. The substrate layer has a characteristic impedance of 10 MRayl, and is $0.75\lambda$ thick at 3 MHz. The backing layer is assumed acoustically infinite, i.e. reflected waves can be neglected due to internal absorption, with a characteristic impedance of 0.5 MRayl. The matching layer 407 has a characteristic impedance of 4.3 MRayl and a thickness of $0.37\lambda$ at 3 MHz, while the acoustic matching layer 408 has a characteristic impedance of 2.33 MRayl and a thickness of $0.55\lambda$ at 3 MHz.

Figure 5A:
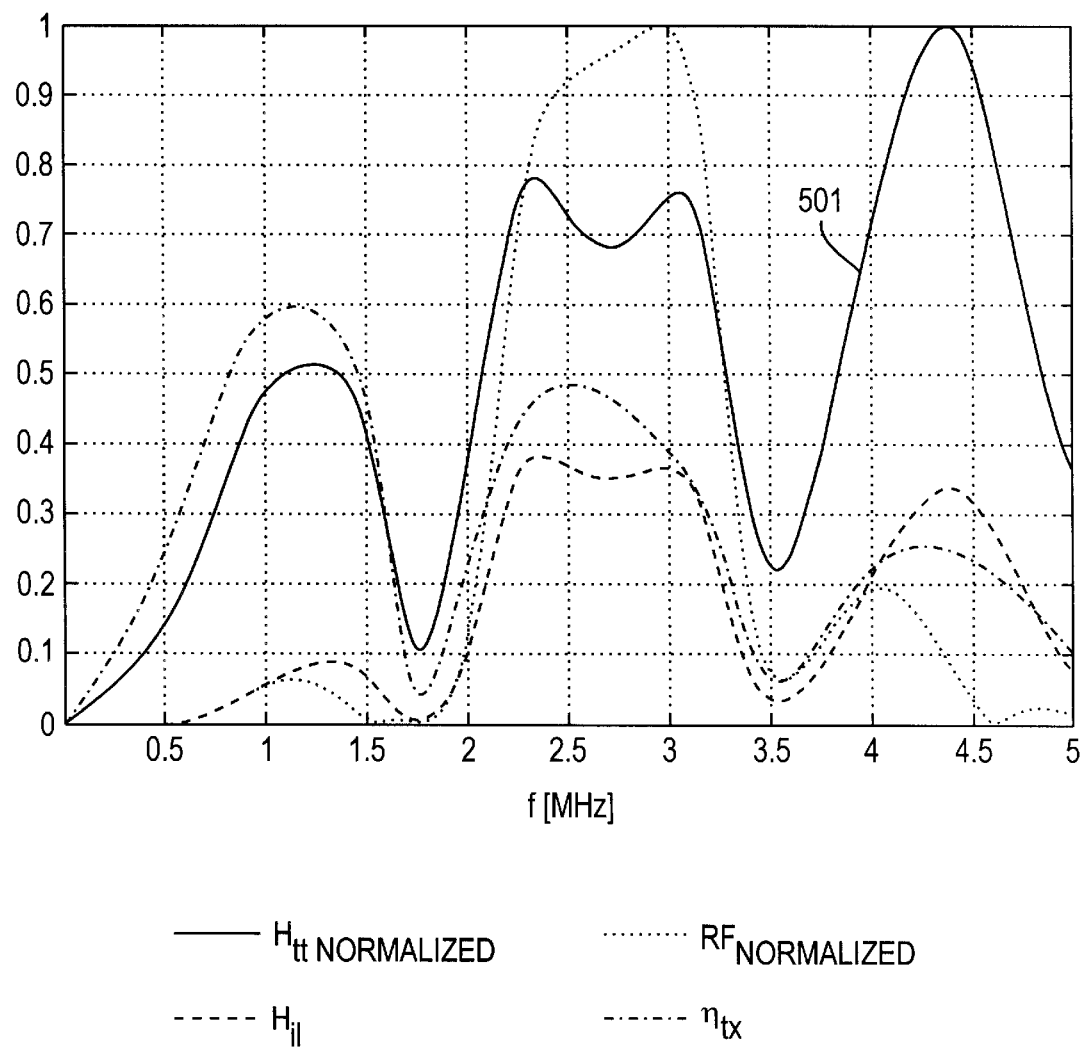
FIG. 5a shows the frequency transfer function from electric drive voltage to front face vibration velocity for one selection of electrodes of the transducer in FIG. 4

The frequency transfer function for the electric drive voltage to the front face vibration velocity, is shown as 501 in FIG. 5a. We see that it exhibits a transfer band around 1 MHz which allows for the transfer of a short pulse with center frequency $f_0=0.8$ MHz, and another effective band between 2 and 3.4 MHz which allows for reception around the $3f_0=2.4$ MHz and $4f_0=3.2$ MHz. We also note that the transfer function has a dip around 1.6 MHz, which attenuates both transmission and reception of the $2^{nd}$ harmonic band around $2f_0$.

Figure 5B:
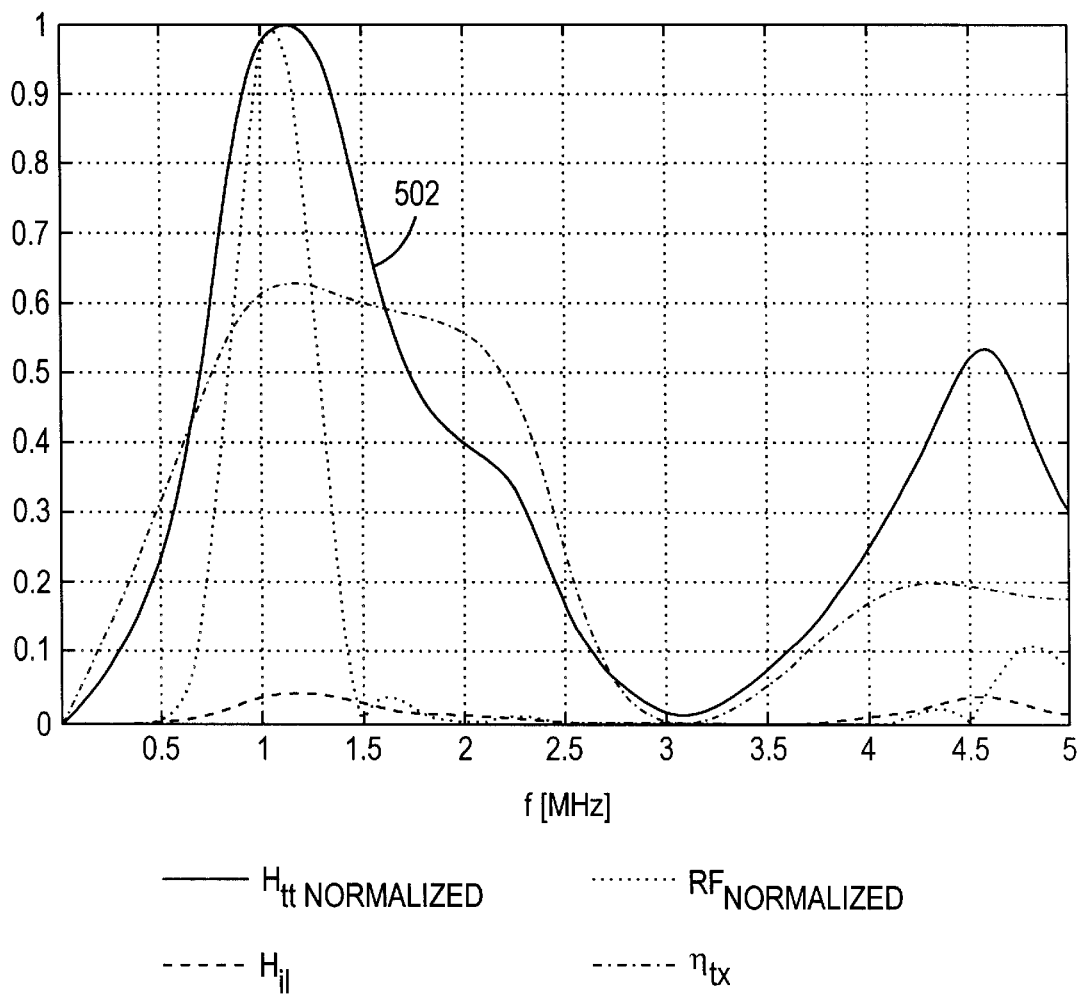
FIG. 5b shows the same transfer function for another selection of electrodes.

A modification of this transducer design that has improved transmit efficiency, is to use the active electroacoustic material also for the substrate layer with the added electrode 409, individually divided for each transducer element. Applying the transmit voltage between electrodes 409 and 402, produces a frequency transfer function from electric voltage to front face vibration velocity shown as 502 in FIG. 5b. This coupling improves the transmit efficiency at 1 MHz, and reduces the transmit efficiency for the $3^{rd}$ harmonic component of the transmit voltage at 3 MHz. This filtering gives a leaner requirement of frequency cleanness of the transmit voltage compared to the transfer function in FIG. 5a, where minor $3^{rd}$ harmonic frequencies in the electric transmit drive voltage will be efficiently transmitted. For receiving frequency components around $3f_0$ and $4f_0$, one would pick up the receiving voltage between electrodes 403 and 402, with a frequency transfer function as in FIG. 5a.

These electrodes can also be used to transmit ultrasound pulses with frequencies in the range 2–3.4 MHz and receive frequencies in the same range for $1^{st}$ harmonic imaging. The structure can also be used to transmit pulses with center frequency around 1.35 MHz and receive $2^{nd}$ harmonic frequencies around 2.7 MHz.

One should note that the layer parameters can be varied for further improvement of the transducer performance. The inventive aspect of the design, is that adequate transfer functions of the assembly is obtained with minimal damping of the transducer. This is achieved with minimizing the characteristic impedance of the backing, and utilizing a substrate layer to provide transducer vibration resonances both in the transmit and the receive bands. One should also note, that by scaling the layer thicknesses, the transfer bands of FIGS. 5a and 5b can be moved proportionally up or down in frequency.

Figure 6A:
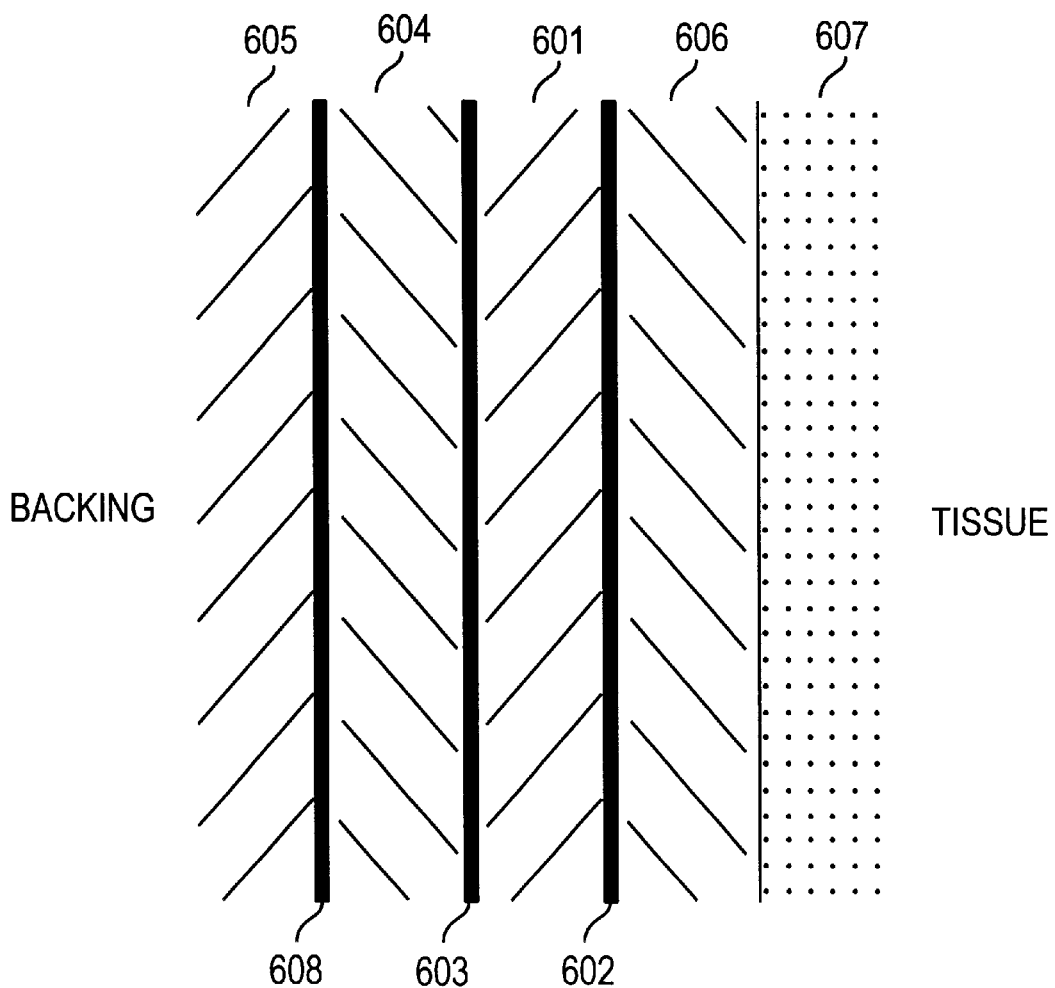
FIG. 6a is a cross section of another layered transducer design with low damping due to high backing impedance, being able to transmit an ultrasound pressure pulse with limited frequency band around $f_0$, and receive back scattered signal in a frequency band around $3f_0$ and/or $4f_0$.

A low damped transducer can also be obtained by using a backing material with characteristic impedance much higher then the impedance of the electro-acoustic active layer. A design using this principle is shown in FIG. 6a, where 601 shows the active electro-acoustic layer with a front electrode 602 and a back electrode 603. The active layer is mounted on a substrate layer 604 with close to the same characteristic impedance as the active layer, and the substrate layer is mounted on the high impedance backing material 605, sufficiently absorbing that reflections from the far end of the backing can be neglected. The Figure shows the use of a single matching layer 606 for coupling of the acoustic power to the tissue 607. An optional electrode 608 at the back of the substrate when this is also made of electro-acoustic material, is also shown.

As for the low impedance backing, one should note that the "substrate" layer 604 could also with the high impedance backing be mounted in front of the active layer, to form a composite layer with high acoustic impedance that gives a composite contribution to the resonances of the transducer.

Figure 6B:
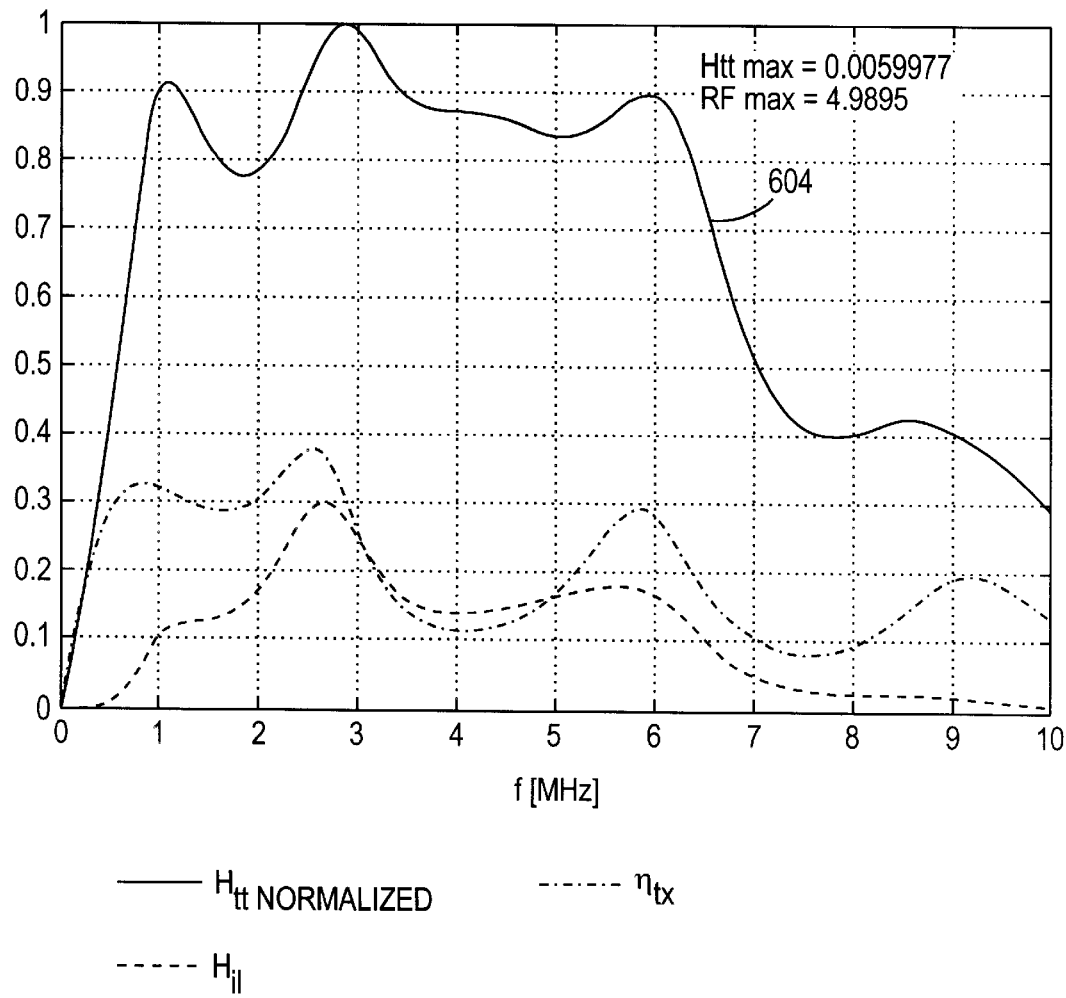
FIG. 6b shows the frequency transfer function from electric drive voltage to front face vibration velocity for one selection of electrodes of the transducer (the transducer is also useful for $1^{st}$ and $2^{nd}$ harmonic imaging)

A typical choice of materials for active layer and substrate layer is the same as for the design in FIG. 5, where the thicknesses now are further optimized for improved performance with the high impedance backing. FIG. 6b shows the frequency transfer function 609 of the voltage to acoustic vibration velocity on the front face, coupling the electric voltage between electrodes 602 and 603. The following material parameters are used: Characteristic impedance of the backing material: 20 MRayl; Characteristic impedance and thickness of the substrate layer: 10 MRayl and $0.15\lambda$ at 3 MHz; Thickness of the active layer $0.27\lambda$ at 3 MHz; Characteristic impedance and thickness of the matching layer: 5 MRayl and $0.375\lambda$ at 3 MHz. We see that an active 3 dB band of the transducer from 0.75 to 6.5 MHz is obtained, which is a relative bandwidth of 155% around a center frequency of 3.6 MHz.

Figure 6C:
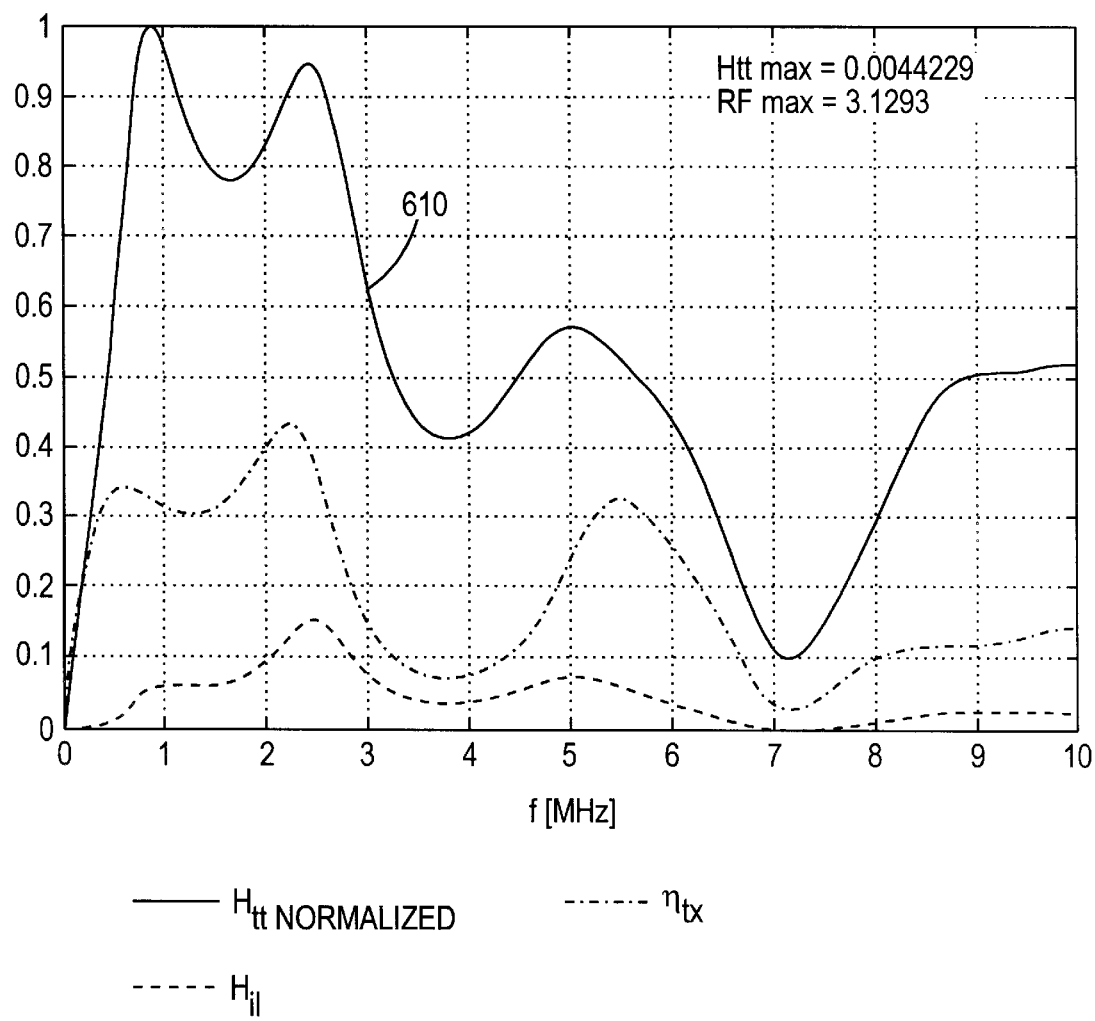
FIG. 6c shows the frequency transfer function from electric drive voltage to the front face vibration velocity for another selection of electrodes in the transducer.

Applying a drive voltage between the back electrode 608 and the front electrode 602, with an electro-acoustic active substrate layer, gives a frequency transfer function of the drive voltage to front face vibration velocity as in 610 of FIG. 6c. This coupling has somewhat higher efficiency in the transmit range than when electrodes 602 and 603 are used, with a lower bandwidth which is adequate to transmit a pulse with frequency components in a band around $f_0$.

With a 20 MRayl backing impedance, the design in FIG. 6a has more internal power losses (damping) than the designs in FIGS. 4a and 5a. Increasing the backing impedance above 20 MRayl reduces the absorption, and presents challenging requirements for acoustic material development.

Figure 7:
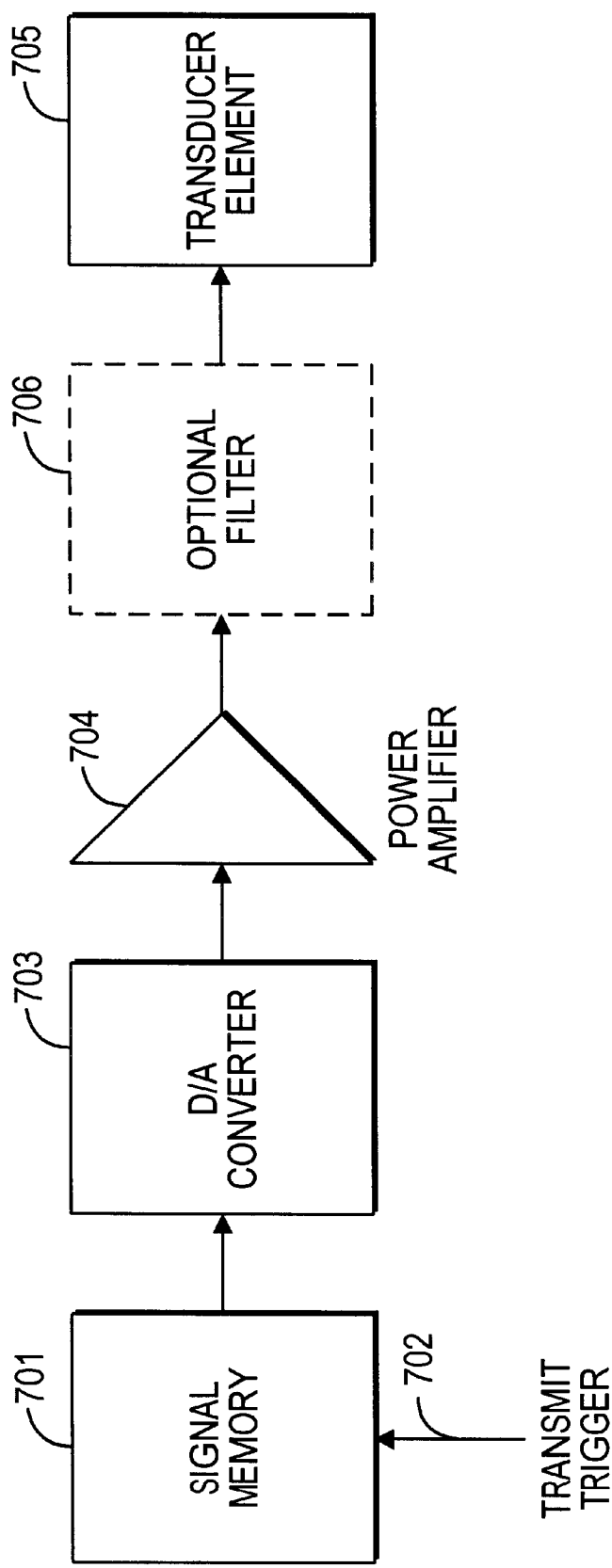
FIG. 7 is a block diagram of a signal generator and power amplifier together with an optional filter, for electric driving of the transducer element with a band-limited voltage oscillation.

Due to the wide bandwidth of both designs in FIGS. 4a and 6a, it is required that the electric drive voltages have a limited bandwidth, so that limited power is transmitted in the $3^{rd}$ and $4^{th}$ harmonic receive bands. A method and implementation for achieving this is shown in FIG. 7, where the transmit pulse form is stored in a digital memory 701. This memory is read out as a signal generator triggered by a transmit trigger signal 702, generated by the control unit 305 of FIG. 3. The digital memory output is fed to a digital to analog converter 703 that drives a linear power amplifier 704, that further drives the transducer array element 705. Pulse distortion by non-linearity of the power amplifier, can optionally be reduced in an output filter 706 between the amplifier and the transducer element. Using the electrodes for the low bandwidth coupling in FIGS. 4–6, requires less frequency cleanness of the transducer drive voltage, as some bandpass filtering occurs directly in the transmit transducer.

The non-linear scattering from contrast agent is more sensitive to the amplitude of the incident pulse than the linear tissue scattering. For harmonic imaging of the contrast agent with comparable conditions over a larger depth range, special requirements must be put on incident amplitude of the transmit beam, which according to the invention is obtained by matching the transmit aperture and the transmit focus to the actual absorption in the tissue, so that the amplitude of the incident pressure pulse is practically constant at all ranges. One method, according to the invention, to obtain such a matching, is to start with preset transmit beam aperture and focussing according to a preset and selectable absorption per unit depth and frequency. The depth variable receiver gain is then adjusted so that the $1^{st}$ harmonic scattered signal from the tissue and contrast agent is constant with depth. The absorption is approximately proportional to the frequency, which gives a first harmonic gain level $g_1(z)$ $$\ln g_1(z) = 2 f_0 \int_0^z d\varsigma a(\varsigma) + \ln G_1$$

where $a(z)$ is the absorption per unit frequency and depth, and $G_1$ is a gain level. For the nth harmonic component, the gain variation $g_n(z)$ is ideally set to $$\ln g_n(z) = (n+1) f_0 \int_0^z d\varsigma a(\varsigma) + \ln G_n$$

where $G_n$ is a gain level, and we have assumed that the attenuation from the transducer to the scatterer is given by the $1^{st}$ harmonic absorption, while the absorption from the scatterer to the transducer is given by the nth harmonic absorption. The far-field focusing and aperture of the transmit beam is then adjusted in steps iteratively where the receiver gain is adjusted as above for each step, so that the amplitude of the nth harmonic component from the contrast is independent of depth from regions where the contrast agent concentration is similar, like in the blood pools.

Figure 8A:
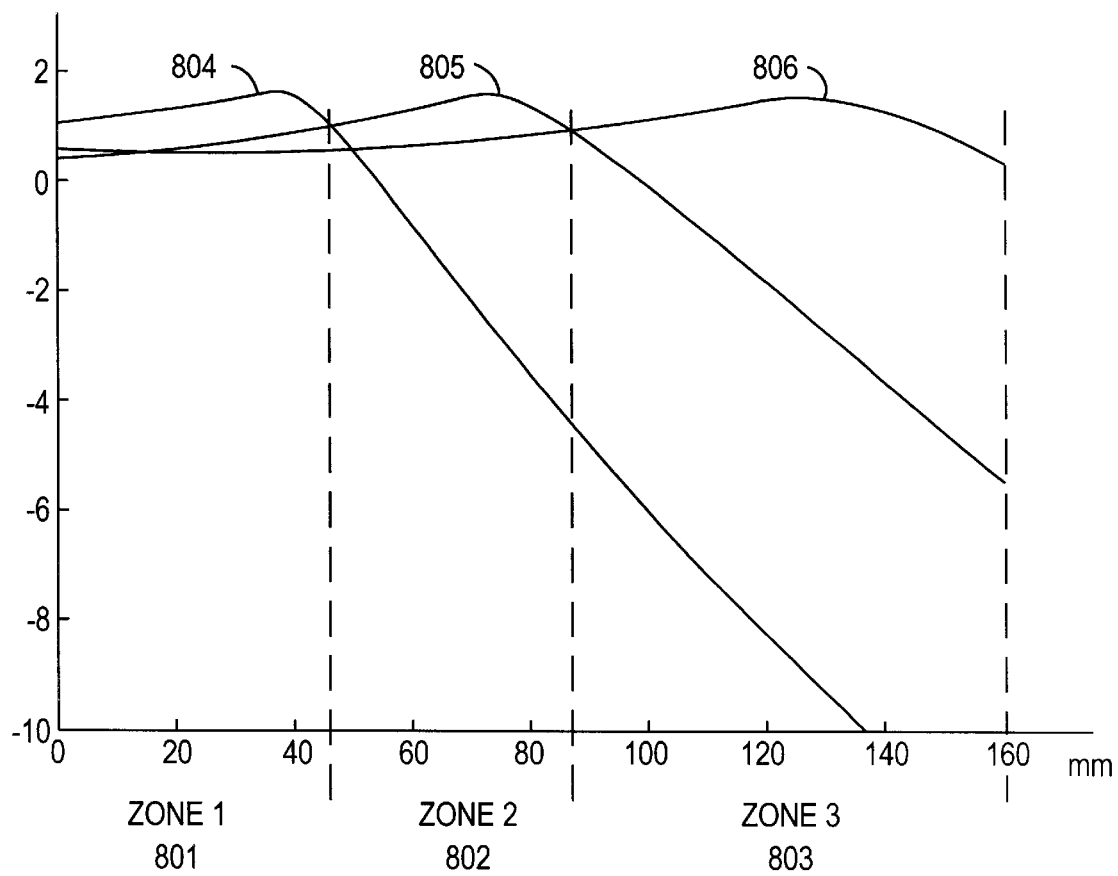
FIGS. 8a and 8b are schematic depictions showing adequate selection of transmit amplitudes, foci, and apertures of transmit pulses for several sub ranges can be used to obtain practically constant incident pulse amplitude and width for a large depth range.
Figure 8B:
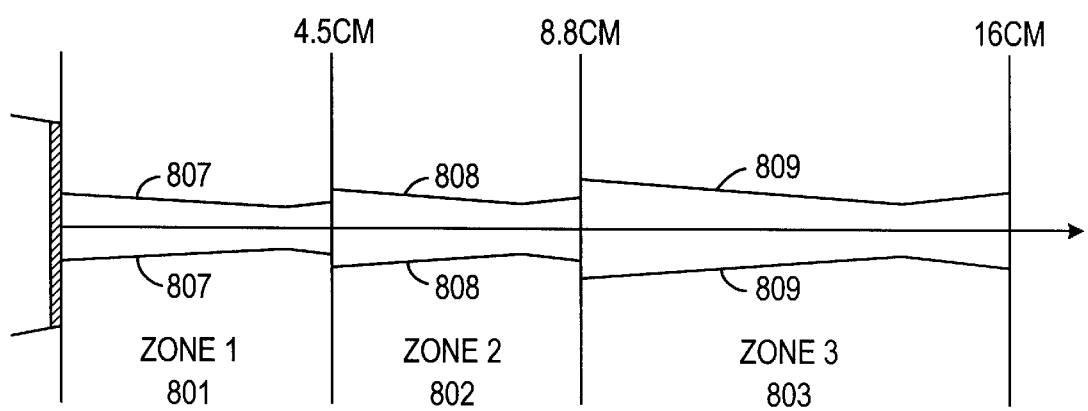

An example of such an equalization of the incident pressure amplitude with depth, is shown in FIGS. 8a and 8b for $f_0$=0.9 MHz and a ~0.4 dB/cmMHz. In this particular example, a total image range of 0–16 cm is subdivided into 3 sub ranges 801, 802, 803, where each sub range is imaged with a separate transmit pulse with different transmit apertures, amplitudes and foci. FIG. 8a shows the axial amplitude of the three transmit pulses, while FIG. 8b shows approximate width of the transmit beams in the 3 zones.

In this particular example a circular transmit aperture is used. The first zone 801 is imaged with a transmit aperture diameter of 17 mm with the transmit focus at 185 mm, giving the amplitude variation 804 with depth. The second zone 802 is imaged with a transmit aperture diameter of 26 mm with the transmit focus at 202 mm, giving the amplitude variation 805 with depth. The third zone 803 is imaged with a transmit aperture diameter of 38 mm with the transmit focus at 265 mm, giving the amplitude variation 806 with depth. Approximate width of the beams in the zones are indicated with the lines 807 for the $1^{st}$ zone, 808 for the $2^{nd}$ zone, and 809 for the $3^{rd}$ zone.

Other variations of the transmit zones, apertures, and foci can be used, according to the invention. We note that the beam for the $3^{rd}$ zone has close to constant amplitude for the whole image range, but it gets a large width at low ranges. This can produce problems with interference from the contrast agent signal from the blood pools in the heart cavities, in the imaging of contrast agent in the myocardium. It is in such a situation an advantage to use the narrower transmit beams for imaging in the other zones. However, where the near-range width of the transmit beam is not a problem, one can use a single transmit beam for imaging the whole range.

Figure 9:
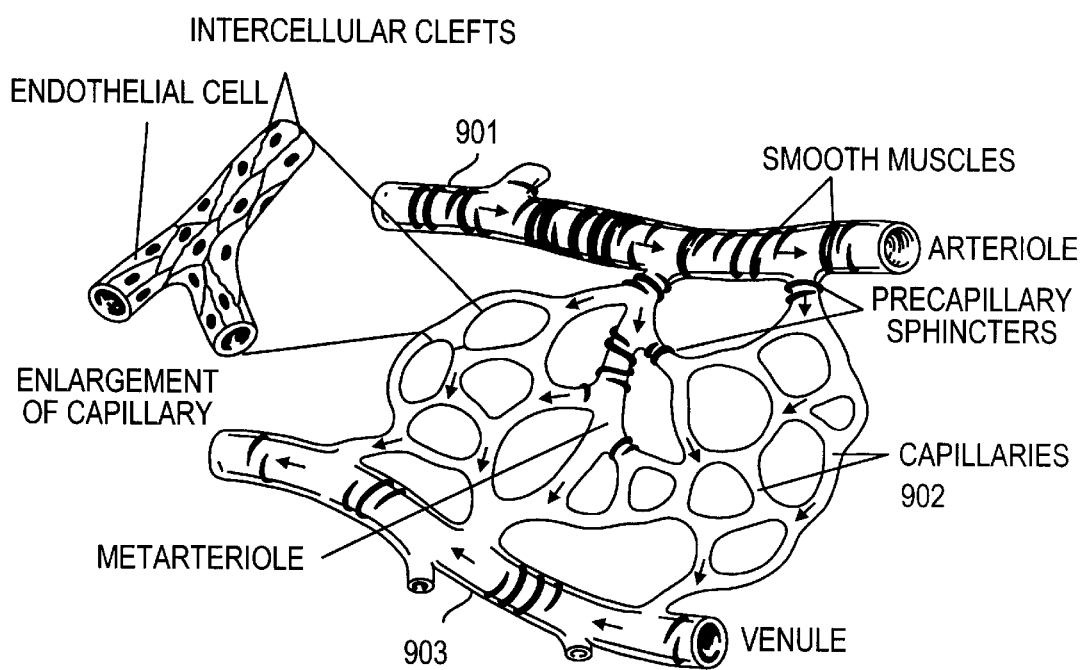
FIG. 9 is a schematic depiction of how the inflow from one artery branches into capillaries that gives the local blood perfusion through the tissue, and finally converges into a vein.

The perfusion of blood through a tissue is illustrated in FIG. 9, where 901 shows a larger vessel that feeds the region of the tissue with blood. The inflow vessel branches into a capillary system 902 through which the tissue is fed with oxygen and nutrition, and metabolic byproducts are removed. The capillary system converges into the venous system 903 that carries the blood away from the tissue.

The arterial inflow of blood is a source, and the venous outflow is a sink of contrast agent into the tissue. The arterial and the venous blood flow is normally the same, and with no other sources or sinks, the concentration of contrast agent in the tissue is in the stationary situation is a product of the volume concentration of blood in the tissue, and the concentration of contrast agent bubbles in the inflowing blood. The perfusion through the tissue describes the volume of blood that flows through a unit volume of tissue per unit time, and is usually measured in $s^{-1}$. We see that when arterial inflow and venous outflow are the only source and sink of contrast agent, the concentration of contrast agent in the tissue is in the stationary situation practically independent of the perfusion through the tissue, until close to complete blockage in the inflow vessel occurs. When perfusion is limited by a stenoses in a coronary artery, the blood volume in the tissue will even increase due to increased diameter of the resistance vessels.

As the detailed positions of the contrast agent bubbles are random, the power of the back-scattered signal from a sample volume will be proportional to the number of contrast agent bubbles in the volume. The signal power is therefore proportional to the product of the concentration of contrast agent bubbles in the volume and the size of the sample volume, which is determined by the length of the received pulse from a bubble, and the width of the combined transmit/receive beam. Hence, in a stationary situation, the signal power will be little influenced by the perfusion through the tissue until close to complete blockage of the perfusion occurs.

However, in the transient filling period of contrast agent into the tissue, the filling time will increase with low perfusion, and the signal amplitude will reflect the perfusion rate, as shown below. Similar effects can also be obtained by partial or complete destruction of the contrast agent with incident ultrasound pulses, where the degree of destruction depends on the amplitude, frequency, pulse length, and other parameters of the pulse.

Such pulse destruction introduces an extra sink of contrast agent in the tissue, where the contrast agent concentration in the tissue, C (#bubbles/ml), will depend on the perfusion rate p ($s^{-1}$), the contrast agent concentration in the inflowing blood, $C_{in}$ (#bubbles/ml), the blood concentration in the tissue, $C_b$ (ml/ml) and the destruction rate q ($s^{-1}$). The relationship can be expressed by the following differential equation $$dC/dt = p\, C_b C_{in} - pC - qC$$

which in the stationary situation when dC/dt=0 gives $$C_{stat} = C_b C_{in} p/(p+q)$$

We hence see that with destruction rate q>0, reduced perfusion gives a drop in $C_{stat}$. This analysis then shows that introducing a bubble destruction rate q, makes it possible to observe regional reduction in the perfusion rate as a drop in the signal power from this region.

With very high amplitude of the incident pulses, one can destroy practically all contrast agent in the imaged region. The refilling of contrast agent into the tissue then follows the following curve $$dC/dt + pC = p C_b C_{in} \quad C(t) = C_b C_{in}(1 - e^{-pt})$$

Figure 10:
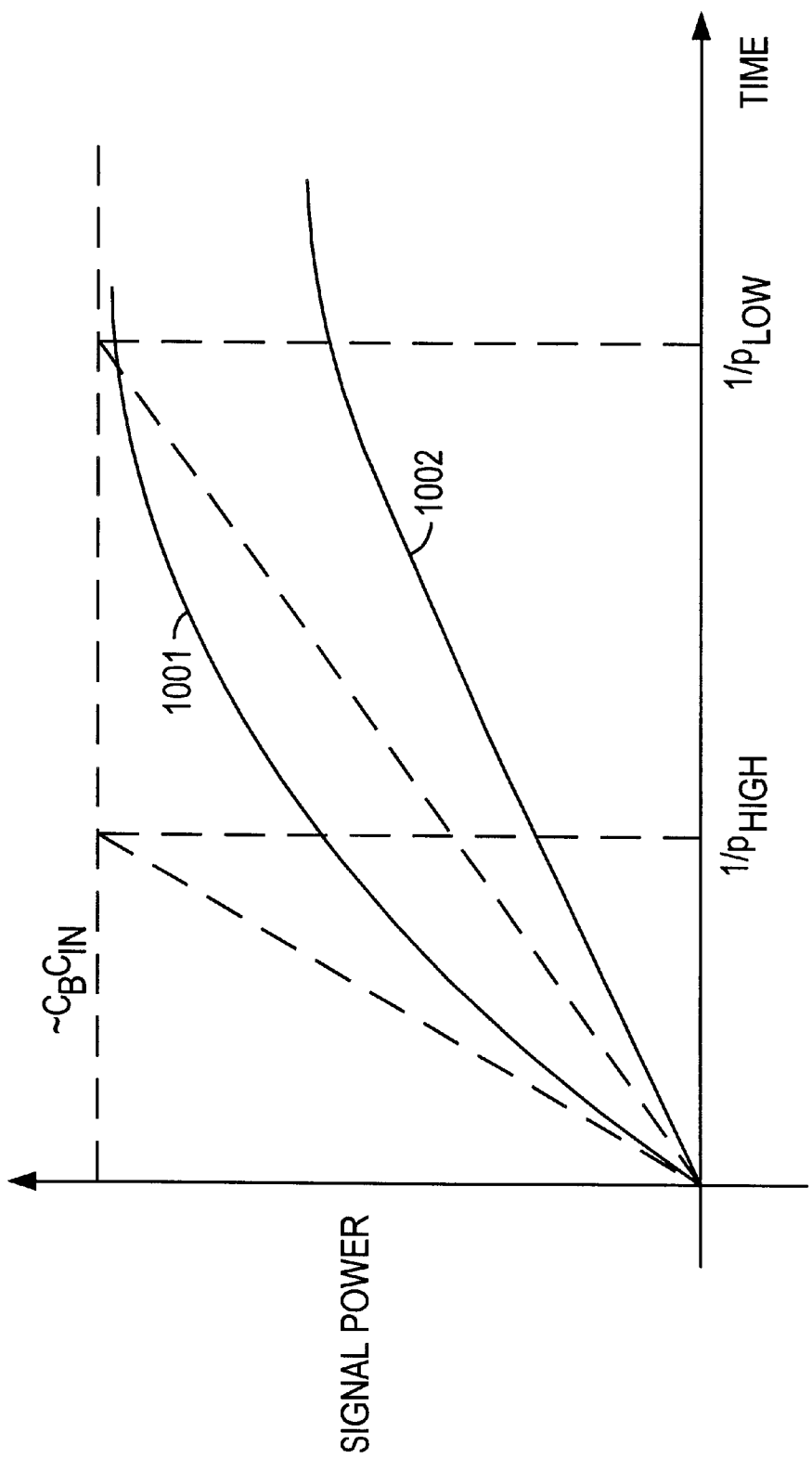
FIG. 10 shows how the filling curves of contrast agent concentration into a tissue region depend on the blood perfusion through the region.

The inflow time constant is 1/p, and for high perfusion rate we get a refilling curve of the contrast agent concentration C(t) as 1001 in FIG. 10, compared to the refilling curve 1002 for low perfusion rate. Hence, one can measure the regional perfusion rate from the refilling time of contrast agent into the region, after complete destruction of the contrast agent in the region. One should then measure the contrast agent concentration at times of equal contraction in the myocardium, preferably in the diastolic period when the myocardium is relaxed. One can then use ECG (electrocardiogram) triggered timing of both the contrast agent destruction and the signal power detection for measurement of the regional refilling times.

Partial bubble destruction by the transmitted pulses can also be used to further enhance the contrast agent signal above the tissue signal, by transmitting several pulses in the same beam direction. The bubble destruction will then introduce a reduced correlation time of the contrast agent signal compared to the tissue signal. The tissue signal can then be relatively attenuated by high-pass filtering of the back-scattered signal along the pulse number coordinate.

The relative blood volume in the myocardium is ~7%. With even concentration of contrast agent in the blood, the signal power from the myocardium is hence ~−12 dB of the signal power from the blood pools in the heart cavities. Sidelobes of the image beam together with limited range resolution in the ultrasound image, hence, will give a corroboration of the signal from the heart cavities into the signal from the myocardium. This gives a lower threshold for the myocardial contrast agent that can be discriminated in the myocardial regions that are corroborated by the signal from the blood.

To reduce this signal corroboration, one can utilize that the blood in the heart cavities at times during the cardiac cycle is moving much faster than the blood in the myocardium. Utilizing the relationship between the back scattered signal from more than one pulse with so low incident amplitude that bubble destruction is avoided, one can reduce the signal amplitude from the faster moving blood. One example of such processing, is to average the received radio frequency signal at each range and beam direction for N pulses, which will attenuate signal components from scatterers with high velocity, compared to those from scatterers with lower velocity. This processing can be done in the Advanced processing unit 310 of FIG. 3. For maximal suppression of the contrast agent signal from the heart cavities, one should carry through this processing and imaging during the period of the heart cycle when the blood in the cavities moves fastest, the timing of which can be selected from ECG-triggering.

For good radial resolution in the final harmonic image, it is important that the backscattered pulse from the contrast agent bubble is as short as possible. This is achieved through two mechanisms: 1) The transmitted pulse centered around $f_0$ must be as short as possible, while limiting the bandwidth of significant frequency components in the pulse. 2) For a short incident pulse, the length of the scattered pulse will depend on the polarity of the incident pressure pulse. The reason for this is that the bubble produces a particularly strong, non-linear and resonant oscillation in the scattered pulse at the turn of the radius oscillation at its minimum. This occurs shortly after the incident pressure pulse swings from negative to positive pressure. This non-linear oscillation is the main source of non-linear distortion in the scattering from contrast agent bubbles. For short incident pulses, the number of significant negative to positive pressure swings in the incident pulse depends on the polarity of the pulse, and the length of the 2nd and higher harmonic components in the scattered pulse hence depends on the polarity of the incident pulse.

Thus, while there have shown and described and pointed out fundamental novel features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for detection of ultrasound contrast agent in soft tissue, utilizing an ultrasound transmit beam former and transducer array assembly that transmits directive, focused ultrasound pressure pulses with steerable transmit amplitude, transmit aperture, transmit focus, and transmit direction, and with temporal frequency components within a limited frequency band B centered at $f_0$, towards the region of soft tissue that contains ultrasound contrast agent bubbles, arranging transmit pulse parameters, possibly using multiple transmit pulses, so that the incident pressure pulse that is utilized for imaging of the contrast agent for a particular depth, has minimal variation over an actual image range, receiving a non-linearly distorted, back-scattered ultrasound signal from both the tissue and the ultrasound contrast agent bubbles with the same ultrasound transducer array assembly and passing received array element signals through a receiver beamformer that has a steerable spatially directive receiver sensitivity, the transducer array assembly having high sensitivity at least at a receive band of frequencies centered at $3f_0$ and/or $4f_0$ or sub-harmonic frequencies for maximal sensitivity of the distorted, non-linearly scattered signal from the contrast agent bubbles, filtering a received signal to attenuate at least the $1^{st}$ and $2^{nd}$ harmonic components of a transmitted band in the back scattered signal so that solely $3^{rd}$, $4^{th}$ or sub-harmonic components of the back scattered signal from the contrast agent, or combinations thereof, is retrieved, and using the filtered signal for detection of ultrasound contrast agent bubbles buried within the tissue, for imaging of contrast agent bubbles in the tissue.

2. A method according to claim 1, where the depth variation of the incident pressure pulse amplitude in the absorbing tissue is minimized by positioning the transmit focus deeper than the image range and adjusting the transmit aperture for close to constant incident pressure amplitude over the actual image range.

3. A method according to claim 1, where the width of the incident beam at each location is reduced, and the depth variation of and amplitude of the incident pressure pulse is minimized by dividing the total imaged depth range into sub-ranges, where a separate transmit pulse is used to interrogate each sub-range consecutively in time, arranging the transmit focus, the transmit aperture, and the transmit amplitude for each pulse so that the pressure pulse amplitude incident on the contrast agent bubbles at their location in the absorbing tissue is practically equal for each sub range.

4. A method according to claim 2, where the back-scattered amplitude in both the $1^{st}$ and the nth harmonic frequency range is used to adjust the transmit focus and aperture for close to constant incident pressure amplitude with depth.

5. A method according to claim 4, where the back-scattered amplitude in both the $1^{st}$ and the nth harmonic frequency range is used to adjust both the depth variable receiver gain and the transmit focus and aperture for close to constant incident pressure amplitude with depth.

6. A method according to claim 1, where the transmitted center frequency $f_0$ is less than 1 MHz.

7. A method according to claim 1, where minimal range resolution in the harmonic image is obtained by using a short transmit pulse with a polarity that minimizes the length of the transmitted pulse.

8. A method according to claim 1, where improved sensitivity of the receiving transducer assembly in the receive band is facilitated by using a backing mount of the transducer with characteristic acoustic impedance less 30% of that of the active electro-acoustic layer.

9. A method according to claim 1, where improved sensitivity of the receiving transducer assembly in the receive band is facilitated by using a backing mount of the transducer with characteristic acoustic impedance greater than 150% of that of the active electro-acoustic layer.

10. A method according to claim 1, where improved sensitivity of the receiving transducer assembly in the receive band is facilitated by making the transducer assembly resonant in this band.

11. A method according to claim 1, where the ultrasound transducer array is composed of an electro-acoustic active layer divided into several transducer elements with a front and a back face, a $1^{st}$ thin electrode layer covering the front face, and a $2^{nd}$ thin electrode layer covering the back face, the electrodes being electrically connected to electric terminals for coupling of energy between the electric terminals and acoustic vibrations in the transducer elements, the thickness of the active layer being less than $\lambda_o/2$ where $\lambda_o=c/f_o$, an added acoustic layer with approximately the same acoustic properties as the active layer, mounted on the back or front of the active layer to form a composite layer with high acoustic impedance, the thickness of the layer being less than $\lambda_o$, the composite layer being mounted on an acoustically absorbing backing with acoustic impedance much lower than the two layers, at least one acoustic matching layer mounted on the front face of the composite layer and acoustically in contact with the tissue or other load material contacting to the tissue, where the acoustic properties and thicknesses of the macthing layers are adjusted to facilitate improved acoustic power transfer to and from the tissue, and wide bandwidth of the electro-acoustic transfer function, to transmit a band-limited ultrasound pulse centered at $f_o$ into the tissue, and receive backscattered ultrasound pulses in sub, $3^{rd}$ or $4^{th}$ harmonic component, or combinations thereof, of the transmit band.

12. A method according to claim 11, where the added acoustic layer also is electro-acoustically active and divided into individual transducer elements with common faces to the first transducer elements of claim 11, with a third, thin electrode layer on the opposite faces of the elements, which can be combined with the $2^{nd}$ or the $1^{st}$ electrodes of claim 11 for coupling of energy between the electric terminals of the electrodes and acoustic vibrations in the combined transducer elements.

13. A method according to claim 12, where two of the 3 electrode layers are connected to the transmit amplifiers to transmit the acoustic pulse, and another two of the 3 electrode layers are coupled to the receiver amplifiers to receive the back scattered acoustic energy from the contrast agent bubbles.

14. A method according to claim 1, where the ultrasound transducer array is composed of an electro-acoustic active layer divided into several transducer elements with a front and a back face, a $1^{st}$ thin electrode layer covering the front face, and a $2^{nd}$ thin electrode layer covering the back face, the electrodes being electrically connected to electric terminals for coupling of energy between the electric terminals and acoustic vibrations in the transducer elements, the thickness of the active layer being less than $\lambda_0/2$, an added acoustic layer with approximately the same acoustic properties as the active layer, mounted on the back or front of the active layer to form a composite layer with high acoustic impedance, the thickness of the layer being less than $\lambda_o$, the composite layer being mounted on an acoustically absorbing backing with acoustic impedance much higher than the two layers, at least one acoustic matching layer mounted on the front face of the composite layer and acoustically in contact with the tissue or other load material contacting to the tissue, where the acoustic properties and thicknesses of the macthing layers are adjusted to facilitate improved acoustic power transfer to and from the tissue, and wide bandwidth of the electro-acoustic transfer function, to transmit a band-limited ultrasound pulse centered at $f_0$ into the tissue, and receive backscattered ultrasound pulses in sub, $3^{rd}$ or $4^{th}$ harmonic component, or combinations thereof, of the transmit band.

15. A method according to claim 14, where the added acoustic layer also is electro-acoustically active and divided into individual transducer elements with common faces to the first transducer elements of claim 14, with a third, thin electrode layer on the opposite faces of the elements, which can be combined with the $2^{nd}$ or the $1^{st}$ electrodes of claim 14 for coupling of energy between the electric terminals of the electrodes and acoustic vibrations in the transducer combined transducer elements.

16. A method according to claim 15, where two of the 3 electrode layers are connected to the transmit amplifiers to transmit the acoustic pulse, and another two of the 3 electrode layers are coupled to the receiver amplifiers to receive the back scattered acoustic energy from the contrast agent bubbles.

17. A method according to claim 1 further includes the step for quantitating regional variation in tissue blood perfusion, where the ultrasound contrast agent in the tissue is destroyed uniformly with depth and direction in the tissue with a controllable degree, during the imaging process of the backscattered signal power from contrast agent in the tissue.

18. A method for quantitating regional variation in tissue blood perfusion according to claim 17, where partial destruction of the contrast agent is done so that the amplitude of the backscattered signal in the sub, $3^{rd}$ or $4^{th}$ harmonic component of the transmit frequency band gives a regional grading of the perfusion.

19. A method for quantitating regional variation in tissue blood perfusion according to claim 17, where separate destruction pulses are used to controllably destroy the contrast agent uniformly over the whole image field.

20. A method for quantitating regional variation in tissue blood perfusion according to claim 17, where the contrast agent is first fully destroyed in the tissue, and imaging is subsequently done with non-destructive pulses at an adequate time interval after this destruction, that the amplitude of the back-scattered signal in the $3^{rd}$ or $4^{th}$ harmonic component of the transmit frequency band gives a regional grading of the refilling time of blood into the tissue, and hence the blood perfusion through the tissue.

21. A method for quantitating regional variation in tissue blood perfusion according to claim 17, where the timing of the contrast agent destruction is derived from the electro-cardiogram (ECG), and imaging is done at a selected period in the cardiac cycle derived from the ECG.

22. A method for quantifying regional variation in tissue blood perfusion according to claim 19, where the increase in image intensity is followed for many heart cycles after the contrast destruction, to obtain complete re-filling curves of contrast agent into different regions of the tissue, for regional grading of the perfusion into the tissue.

23. A method according to claim 1, where the signal from the contrast agent is further enhanced above the signal from the tissue, in that several pulses are transmitted in the same beam direction, and that the incident amplitude is increased so that partial destruction of the contrast agent occurs for each pulse producing a temporal decorrelation of the contrast agent signal that is different from the tissue signal, so that the tissue signal can be attenuated by filtering the back scattered signal between transmit pulses in the same beam direction.

* * * * *